US012558013B2

(12) United States Patent
Wong et al.

(10) Patent No.:  US 12,558,013 B2
(45) Date of Patent:  Feb. 24, 2026

(54) LOOP CONFIGURATION FOR CARDIAC CATHETER END EFFECTOR

(71) Applicant: Biosense Webster (Israel) Ltd., Yokneam (IL)

(72) Inventors: Kaela Wong, Miami, FL (US); Pieter E. Van Niekerk, Monrovia, CA (US)

(73) Assignee: Biosense Webster (Israel) Ltd., Yokneam (IL)

( * ) Notice:   Subject to any disclaimer, the term of this patent is extended or adjusted under 35 U.S.C. 154(b) by 483 days.

(21) Appl. No.: 17/871,362

(22) Filed:    Jul. 22, 2022

(65)           Prior Publication Data

US 2024/0023865 A1     Jan. 25, 2024

(51) Int. Cl.
    *A61B 18/14*        (2006.01)
    *A61B 5/00*         (2006.01)
    *A61B 5/279*        (2021.01)
(52) U.S. Cl.
    CPC ............ *A61B 5/279* (2021.01); *A61B 5/6856* (2013.01)
(58) Field of Classification Search
    CPC .................. A61B 5/279; A61B 5/6856; A61B 2018/1407; A61N 1/0553
    See application file for complete search history.

(56)              References Cited

U.S. PATENT DOCUMENTS

| | | | |
|---|---|---|---|
| 5,944,022 A | 8/1999 | Nardella et al. | |
| 5,983,126 A | 11/1999 | Wittkampf | |
| 6,023,638 A * | 2/2000 | Swanson .............. | A61B 5/6855 606/41 |
| 6,445,864 B2 | 9/2002 | Jiang et al. | |
| 9,687,166 B2 | 6/2017 | Subramaniam et al. | |
| 11,350,987 B2 | 6/2022 | Pappone et al. | |
| 11,426,111 B2 | 8/2022 | Olson | |
| 11,850,051 B2 | 12/2023 | Selkee et al. | |
| 2015/0105645 A1 * | 4/2015 | Subramaniam ........ | A61B 5/361 600/374 |
| 2016/0374753 A1 * | 12/2016 | Wu ...................... | A61B 5/6859 606/41 |
| 2020/0345262 A1 * | 11/2020 | Selkee ............... | A61B 18/1492 |

FOREIGN PATENT DOCUMENTS

IT      202000020149 A1    2/2022

OTHER PUBLICATIONS

Extended European Search Report for Application No. EP23186876.1, dated Dec. 21, 2023, 8 pages.

* cited by examiner

*Primary Examiner* — Adam Z Minchella
(74) *Attorney, Agent, or Firm* — FBT Gibbons LLP

(57)              ABSTRACT

A catheter for electrophysiology includes a shaft extending along a longitudinal axis to a distal end and an end effector coupled to the distal end of the shaft. The end effector includes a first loop member disposed on a first side of the longitudinal axis, a second loop member disposed on a second side of the longitudinal axis, and a third loop member. The third loop member includes a first spine disposed on the first side of the longitudinal axis. The first spine includes a first plurality of electrodes. The first spine is positioned radially outwardly of the first loop member relative to the longitudinal axis. The third loop member further includes a second spine disposed on the second side of the longitudinal axis. The second spine includes a second plurality of electrodes and is positioned radially outwardly of the second loop member relative to the longitudinal axis.

20 Claims, 5 Drawing Sheets

LOOP CONFIGURATION FOR CARDIAC CATHETER END EFFECTOR

BACKGROUND

Cardiac arrhythmia, such as atrial fibrillation, occurs when regions of cardiac tissue abnormally conduct electric signals to adjacent tissue, thereby disrupting the normal cardiac cycle and causing asynchronous rhythm. Important sources of undesired signals are located in the tissue region, for example, one of the atria or one of the ventricles. Regardless of the sources, unwanted signals are conducted elsewhere through heart tissue where they can initiate or continue arrhythmia.

Procedures for treating arrhythmia include surgically disrupting the origin of the signals causing the arrhythmia, as well as disrupting the conducting pathway for such signals. More recently, it has been found that by mapping the electrical properties of the endocardium and the heart volume, and selectively ablating cardiac tissue by application of energy, it is possible to cease or modify the propagation of unwanted electrical signals from one portion of the heart to another. The ablation process destroys the unwanted electrical pathways by formation of non-conducting lesions.

In this two-step procedure—mapping followed by ablation—electrical activity at points in the heart is typically sensed and measured by advancing a catheter containing one or more electrical sensors into the heart and acquiring data at a multiplicity of points. These data are then utilized to select the target areas at which ablation is to be performed.

For greater mapping resolution, it is desirable for a mapping catheter to provide very high-density signal maps through the use of a multitude of electrodes sensing electrical activity within a small area, for example, a square centimeter. For mapping within an atria or a ventricle (for example, an apex of a ventricle), it is desirable for a catheter to collect larger amounts of data signals within shorter time spans. It is also desirable for such a catheter to be adaptable to different tissue surfaces, for example, flat, curved, irregular or nonplanar surface tissue and be collapsible for atraumatic advancement and withdrawal through a patient's vasculature.

SUMMARY OF THE DISCLOSURE

Various embodiments described herein allow high density mapping and/or ablation of tissue surface in the heart, including an atrium or a ventricle, by virtue of a catheter for electrophysiology applications. The catheter includes a main loop extending along a longitudinal axis on a first plane. The catheter also includes a second loop extending along the longitudinal axis on one side of the longitudinal axis on a second plane generally parallel to the first plane, the second loop being coupled to the main loop proximate a distal portion of the main loop. The catheter also includes a third loop extending along the longitudinal axis on another side of the longitudinal axis on the second plane, the third loop being coupled to the main loop proximate a distal portion of the main loop.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

DETAILED DESCRIPTION FOR MODES OF CARRYING OUT THE INVENTION

Figure 1:
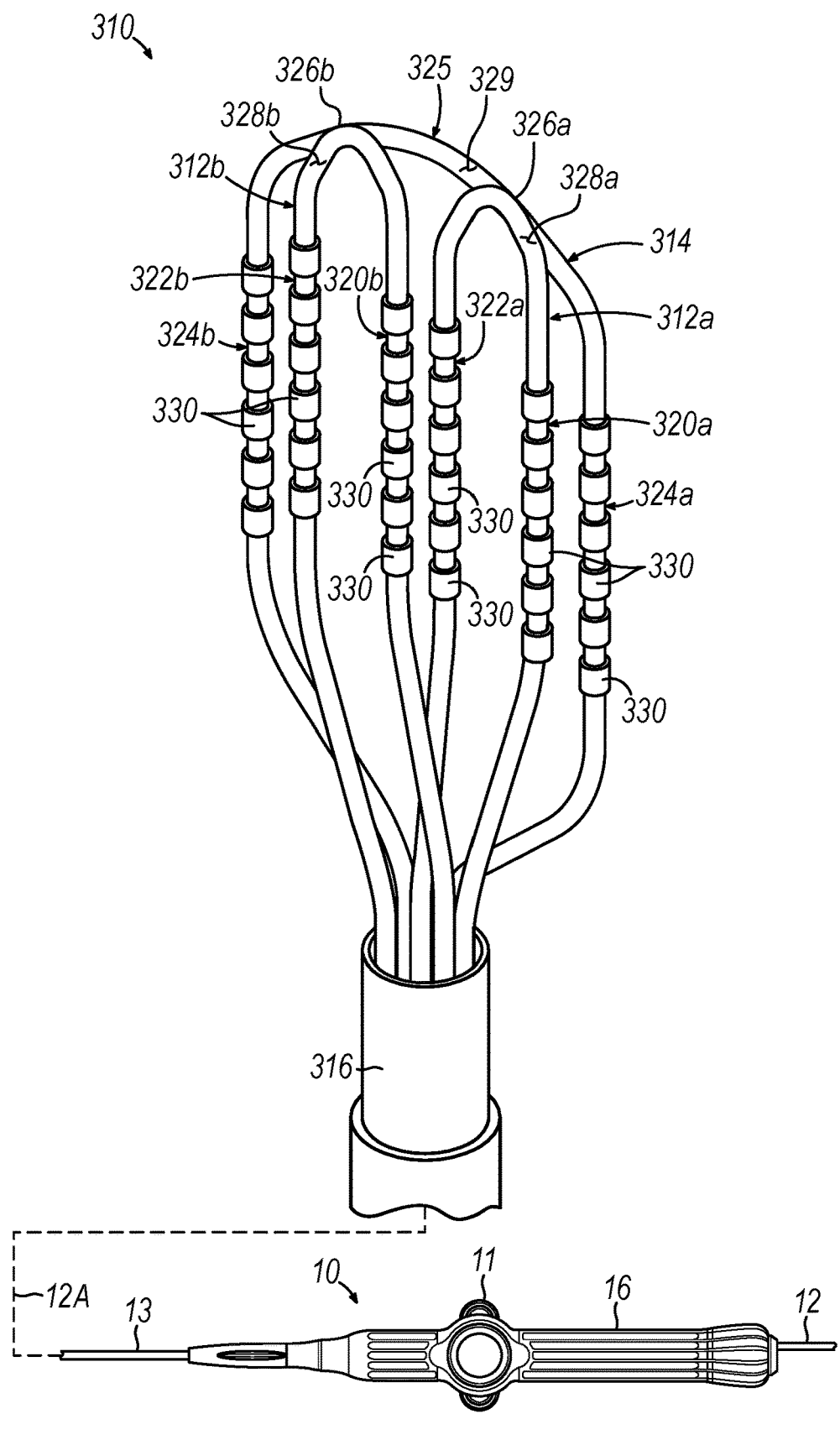
FIG. 1 illustrates a schematic view of an example of a catheter from an end effector at a distal portion of the catheter to the proximal handle, with the end effector including a pair of inner loop members and an outer loop member having a pair of outermost spines that are integrally formed with each other.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g., "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. The term "proximal" and "distal" are used to reference location of various components with respect to the handle which is designated as the most proximal to a user operating the handle.

I. Example of Loop Configuration for a Catheter End Effector

In some procedures, it may be desirable to selectively house an end effector within a tubular sheath and selectively deploy the end effector from the tubular sheath, such that a plurality of (e.g., three) electrode loop members (also referred to as loops) of the end effector are elastically compressed to a collapsed state when the end effector is housed within the tubular sheath, and such that the loops resiliently expand from the collapsed state to an expanded state when the end effector is deployed from the tubular sheath. In addition, or alternatively, it may be desirable to direct the end effector into the tubular sheath using an insertion tool. Therefore, it may be desirable to configure the loops to distribute stress across the loops in a predetermined manner that allows the loops to maintain their elasticity and avoid yielding to plastic deformation, which may otherwise occur when the outermost spines and/or distal segments of the loops are subjected to various stress concentrations, during repeated cycles of deployment and housing of the end effector relative to the tubular sheath and/or repeated cycles of being directed into the tubular sheath via the insertion tool.

In this regard, the loops may each experience two deformation modes upon repeated cycles of deployment and housing: in-plane deformation (also referred to as planar deformation) and out-of-plane deformation. Some cases of planar deformation may include inward bowing of the two outermost spines toward each other such that the two outermost spines collectively define an "hourglass" shape, which may occur when the two outermost spines experience substantially high stress concentrations at or near the apex of their distal curvature upon entry into the tubular sheath. The deformation at the apex caused by the stress concentration at the said apex may result in the lateral straight sections angling inward, resulting in the aforementioned "hourglass" shape. Some cases of out-of-plane deformation may include inward folding of the two outer loops toward each other around the central loop, such as due to the two outermost spines being parts of two separate loops which can move independently of each other, deform, and rotate to curl in the direction of collapse. Such deformation may be referred to as "paddle folding."

Distributing stress across the loops in a predetermined manner that minimizes or eliminates undesirable stress concentrations may inhibit the aforementioned modes of deformation from occurring, such that the loops may consistently and reliably expand from the collapsed state to the desired expanded state in which electrodes of the loops may be spaced apart from each other by predefined distances. It will be appreciated that avoiding inadvertent deviations from such predefined distances when in the expanded state may facilitate consistent and reliable functionality of the electrodes.

Figure 2:
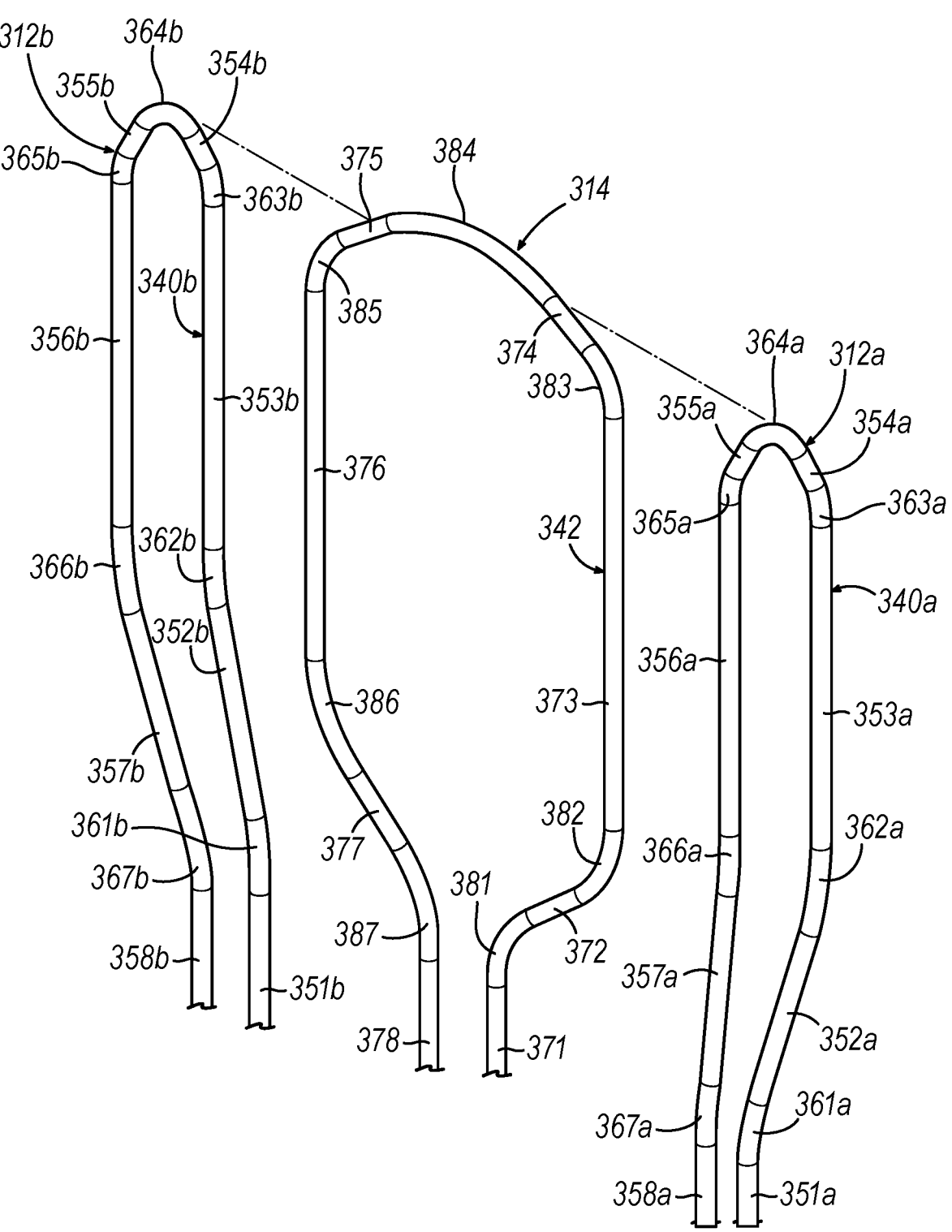
FIG. 2 illustrates an exploded perspective view of the end effector of FIG. 1, with electrodes and covers of the loop members omitted to show elongated structural members of the loop members.
Figure 3:
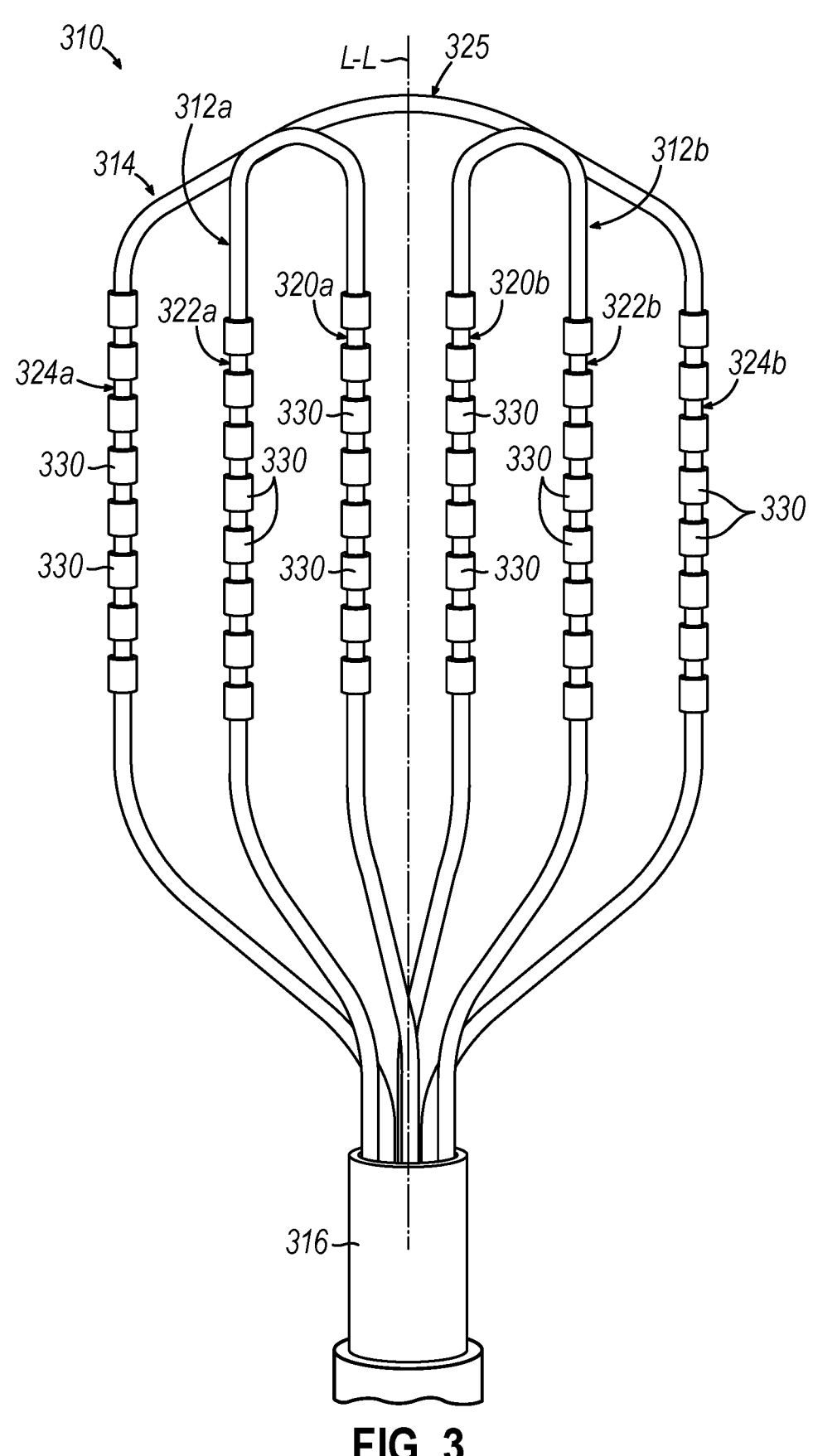
FIG. 3 illustrates a front plan view of the end effector of FIG. 1.

FIGS. 1-4 depict an example of a catheter (10) including an end effector (310) having such a configuration. As shown in FIG. 1, the catheter (10) comprises an elongated catheter body (12) disposed inside a separate intermediate tubular section (13), a distal electrode assembly or end effector (310), and a deflection control handle (16) attached to the proximal end of the catheter body (12). End effector (310) of this example includes first and second inner loop members (312a, 312b) and an outer loop member (314), each extending distally from a base member or shaft (316), which itself extends along longitudinal axis (L-L) (FIG. 3). One or more impedance sensing electrodes (not shown) can be provided on base member (316) to allow for location sensing via impedance location sensing technique, as described in U.S. Pat. No. 5,944,022, entitled "Catheter Positioning System," issued Aug. 31, 1999; U.S. Pat. No. 5,983,126, entitled "Catheter Location System and Method," issued Nov. 9, 1999; and U.S. Pat. No. 6,445,864, entitled "Dispersion Compensating Optical Fiber," issued Sep. 3, 2002. The disclosures of each of these references is incorporated herein by reference, in its entirety. Details of the catheter body (16) can be understood from a review of U.S. Pub. No. 2020/0345262, entitled "Mapping Grid with High Density Electrode Array," published Nov. 5, 2020 (including the description to the handle and particularly FIGS. 2D, 2E and 3 in this prior application), the disclosure of which is incorporated by reference herein, in its entirety. Loop members (312a, 312b, 314) may also be referred to as paddles, loops, and/or electrode loop assemblies.

In the example shown, first and second inner loop members (312a, 312b) are substantially identical to each other and are disposed on either side of longitudinal axis (L-L), radially inwardly of third or central loop member (314). Central loop member (314 or 425) has its spine defining a first plane (P1) that extends through the center of the spines (FIG. 5B) while the center spines of the first and second loop members (312a, 312b or 412a and 412b) define a second plane (P2) (FIG. 5B) spaced apart from the first plane (P1). That is, each plane (P1 or P2) extends through the section area of the respective loop members. In this configuration, it can be seen that the central loop member (425) or inner loop members (412a, 412b) may have the respective outer surfaces of the loop members (425, 412a, 412b) contiguous to a single third plane (P3) extending through the longitudinal axis (L-L). As best shown in FIG. 3, second inner loop member (312b) is identical to first inner loop member (312a) except that second inner loop member (312b) is oriented 180 degrees compared to first inner loop member (312a) with respect to longitudinal axis (L-L). That is, inner loop members (312a, 312b) can be considered to be mirror images of each other. Outer loop member (314) on the other hand is distinct from inner loop members (312a, 312b). More particularly, inner loop members (312a, 312b) each include a corresponding innermost spine member (320a, 320b) and a corresponding intermediate spine member (322a, 322b), while outer loop member (314) includes a pair of outermost spine members (324a, 324b) coupled to each other via a distalmost arch (325). Spine members (320a, 320b, 322a, 322b, 324a, 234b) may also be referred to as spines. In this regard, innermost spines (320a, 320b) are positioned radially inwardly of intermediate spines (322a, 322b) with respect to longitudinal axis (L-L), and outermost spines (324a, 324b) are positioned radially outwardly of intermediate spines (322a, 322b) with respect to longitudinal axis (L-L), at least within the frame of reference of FIG. 3. It will be appreciated that first innermost spine member (320a) is integral with first intermediate spine member (322a) as part of first inner loop (312a) and that second innermost spine member (320b) is integral with second intermediate spine member (322b) as part of second inner loop (312b). Similarly, first outermost spine member (324a) is integral with second outermost spine member (324b) as part of outer loop (314).

As best shown in FIG. 1, inner loop members (312a, 312b) of the present version are each tied to or otherwise couple to outer loop member (314) at respective distal interfaces (326a, 326b). In this regard, inner loop members (312a, 312b) each include a corresponding cover (328a, 328b) while outer loop member (314) includes a corresponding cover (329) contacting covers (328a, 328b) at the respective distal interfaces (326a, 326b). Covers (328a, 328b, 329) may each be electrically insulative, and/or may each include a polymeric material such as polyurethane, for example. In this regard, covers (328a, 328b) in the present version are each joined with cover (329) at the respective distal interfaces (326a, 326b) via heating and reflowing of the polymeric material forming each cover (328a, 328b, 329). In some other versions, inner loop members (312a, 312b) may each be tied to outer loop member (312) at the respective distal interfaces (326a, 326b) via a suture or any other suitable coupling means. Alternatively, inner loop members (312a, 312b) may not be coupled to outer loop member (312) at the respective distal interfaces (326a, 326b).

Loop members (312a, 312b, 314) also each include a corresponding plurality of sensing electrodes (330) disposed on an outer surface of the respective cover (328a, 328b, 329). Electrodes (330) may be configured to provide electrophysiology (EP) mapping, such as to identify tissue regions that should be targeted for ablation. For example, electrodes (330) may monitor electrical signals emanating from conductive endocardial tissues to pinpoint the location of aberrant conductive tissue sites that are responsible for an arrhythmia. By way of example only, electrodes (330) may be configured and operable in accordance with at least some of the teachings of U.S. Pub. No. 2020/0345262, entitled "Mapping Grid with High Density Electrode Array," published Nov. 5, 2020, the disclosure of which is incorporated by reference herein, in its entirety.

FIG. 2 depicts each loop member (312a, 312b, 314) with covers (328a, 328b, 329) and electrodes (330) omitted to show structural members (340a, 340b, 342) of loop members (312a, 312b, 314) underlying the respective covers (328a, 328b, 329). In this regard, each inner loop member (312a, 312b) has a corresponding elongated structural member (340a, 340b) extending continuously through the length of the respective inner loop member (312a, 312b) to and from base member (316), while outer loop member (314) has an elongated structural member (342) extending continuously through the length of outer loop member (314) to and from base member (316). Structural members (340a, 340b, 342) may also be referred to as loop structural members, spine frames, or frames. Structural members (340a, 340b, 342) can each include a biocompatible metal such as stainless steel, cobalt chromium, or nitinol. While structural members (340a, 340b, 342) of the present version are each formed from a single unitary material, each segment of the structural member (340a, 340b) of each inner loop (312a, 312b) may alternatively be discrete components affixed to each other. At least one proximal portion of each structural member (340a, 340b, 342) extends into a distal end portion of base member (316) and is secured thereto. In the example shown, structural members (340a, 340b) of inner loop members (312a, 312b) each have an asymmetric configuration while structural member (342) of outer loop member (314) has a symmetric configuration (e.g., relative to longitudinal axis (L-L)).

With continuing reference to FIG. 2, structural members (340a, 340b) of inner loops (312a, 312b) are each formed as a unitary structural framework defining respective pluralities of segments, such as eight respective linear segments (351a, 351b, 352a, 352b, 353a, 353b, 354a, 354b, 355a, 355b, 356a, 356b, 357a, 357b, 358a, 358b) and seven respective curved segments (361a, 361b, 362a, 362b, 363a, 363b, 364a, 364b, 365a, 365b, 366a, 366b, 367a, 367b). More particularly, structural members (340a, 340b) of inner loops (312a, 312b) each include a respective first linear segment (351a, 351b) extending distally from base member (316) along a generally straight path; a respective first curved segment (361a, 361b) extending along a generally arcuate path and coupling the respective first linear segment (351a, 351b) to a respective second linear segment (352a, 352b) extending distally and transversely outwardly from the respective first curved segment (361a, 361b) along a generally straight path; a respective second curved segment (362a, 362b) extending along a generally arcuate path and coupling the respective second linear segment (352a, 352b) to a respective third linear segment (353a, 353b) extending distally from the respective second curved segment (362a, 362b) along a generally straight path; a respective third curved segment (363a, 363b) extending along a generally arcuate path and coupling the respective third linear segment (353a, 353b) to a respective fourth linear segment (354a, 354b) extending distally and transversely inwardly from the respective third curved segment (363a, 363b) along a generally straight path; a respective fourth curved segment (364a, 364b) extending along a generally arcuate path and coupling the respective four linear segment (354a, 354b) to a respective fifth linear segment (355a, 355b) extending proximally and transversely outwardly from the respective fourth curved segment (364a, 364b) along a generally straight path; a respective fifth curved segment (365a, 365b) extending along a generally arcuate path and coupling the respective fifth linear segment (355a, 355b) to a respective sixth linear segment (356a, 356b) extending proximally from the respective fifth curved segment (365a, 365b) along a generally straight path; a respective sixth curved segment (366a, 366b) extending along a generally arcuate path and coupling the respective sixth linear segment (356a, 356b) to a respective seventh linear segment (357a, 357b) extending proximally and transversely inwardly from the respective sixth curved segment (366a, 366b) along a generally straight path; and a respective seventh curved segment (367a, 367b) extending along a generally arcuate path and coupling the respective seventh linear segment (357a, 357b) to a respective eighth linear segment (358a, 358b) extending proximally from the respective seventh curved segment (367a, 367b) to base member (316) along a generally straight path.

As noted above, structural members (340a, 340b) of inner loop members (312a, 312b) each have an asymmetric configuration. In this regard, second linear segment (352a, 352b) of each inner loop member (312a, 312b) may have a different length from that of the corresponding seventh linear segment (357a, 357b) of the respective inner loop member (312a, 312b), and/or may be oriented at a different angle relative to the corresponding first linear segment (351a, 351b) of the respective inner loop member (312a, 312b) than that at which the corresponding seventh linear segment (357a, 357b) is angled relative to the corresponding eighth linear segment (358a, 358b) of the respective inner loop member (312a, 312b). In addition, or alternatively, third linear segment (353a, 353b) of each inner loop member (312a, 312b) may have a different length from that of the corresponding sixth linear segment (356a, 356b) of the respective inner loop member (312a, 312b). As another example, fourth linear segment (354a, 354b) of each inner loop member (312a, 312b) may have a different length from that of the corresponding fifth linear segment (355a, 355b) of the respective inner loop member (312a, 312b), and/or may be oriented at a different angle relative to the corresponding third linear segment (353a, 353b) of the respective inner loop member (312a, 312b) than that at which the corresponding fifth linear segment (355a, 355b) is angled relative to the corresponding sixth linear segment (356a, 356b) of the respective inner loop member (312a, 312b). It will be appreciated that innermost spine member (320a, 320b) may each be defined, at least in part, by the corresponding third linear segment (353a, 353b) of the respective structural member (340a, 340b), and that intermediate spine members (322a, 322b) may each be defined, at least in part, by the corresponding sixth linear segment (356a, 356b) of the respective structural member (340a, 340b).

With continuing reference to FIG. 2, structural member (342) of outer loop (314) is also formed as a unitary structural framework defining a plurality of segments, such as eight linear segments (371, 372, 373, 374, 375, 376, 377, 378) and seven curved segments (381, 382, 383, 384, 385, 386, 387). More particularly, structural member (342) of outer loop (314) includes a first linear segment (371) extending distally from base member (316) along a generally straight path; a first curved segment (381) extending along a generally arcuate path and coupling first linear segment (371) to a second linear segment (372) extending distally and laterally outwardly from first curved segment (381) along a generally straight path; a second curved segment (382) extending along a generally arcuate path and coupling second linear segment (372) to a third linear segment (373) extending distally from second curved segment (382) along a generally straight path; a third curved segment (383) extending along a generally arcuate path and coupling third linear segment (373) to a fourth linear segment (374) extending distally and laterally inwardly from third curved segment (383) along a generally straight path; a fourth curved segment (384) extending along a generally arcuate path and coupling four linear segment (374) to a fifth linear segment (375) extending proximally and laterally outwardly from fourth curved segment (384) along a generally straight path; a fifth curved segment (385) extending along a generally arcuate path and coupling fifth linear segment (375) to a sixth linear segment (376) extending proximally from fifth curved segment (385) along a generally straight path; a sixth curved segment (386) extending along a generally arcuate path and coupling sixth linear segment (376) to a seventh linear segment (377) extending proximally and laterally inwardly from sixth curved segment (386) along a generally straight path; and a seventh curved segment (387) extending along a generally arcuate path and coupling seventh linear segment (377) to an eighth linear segment (378) extending proximally from seventh curved segment (387) to base member (316) along a generally straight path.

As noted above, structural member (342) of outer loop member (314) has a symmetric configuration (e.g., relative to longitudinal axis L-L)). In this regard, second linear segment (372) may have a same length as that of seventh linear segment (377), and/or may be oriented at a same angle relative to first linear segment (371) as that at which seventh linear segment (377) is angled relative to eighth linear segment (378). In addition, or alternatively, third linear segment (373) may have a same length as that of sixth linear segment (376). As another example, fourth linear segment (374) may have a same length as that of fifth linear segment (375), and/or may be oriented at a same angle relative to third linear segment (373) as that at which fifth linear segment (375) is angled relative to sixth linear segment (376) as described in greater detail below. It will be appreciated that outermost spine members (324a, 324b) may be defined, at least in part, by third and sixth linear segments (373, 376), respectively, of structural member (342), and that distalmost arch (325) may be defined, at least in part, by fourth curved segment (384) and fourth and fifth linear segments (374, 375) of structural member (342).

Figure 4:
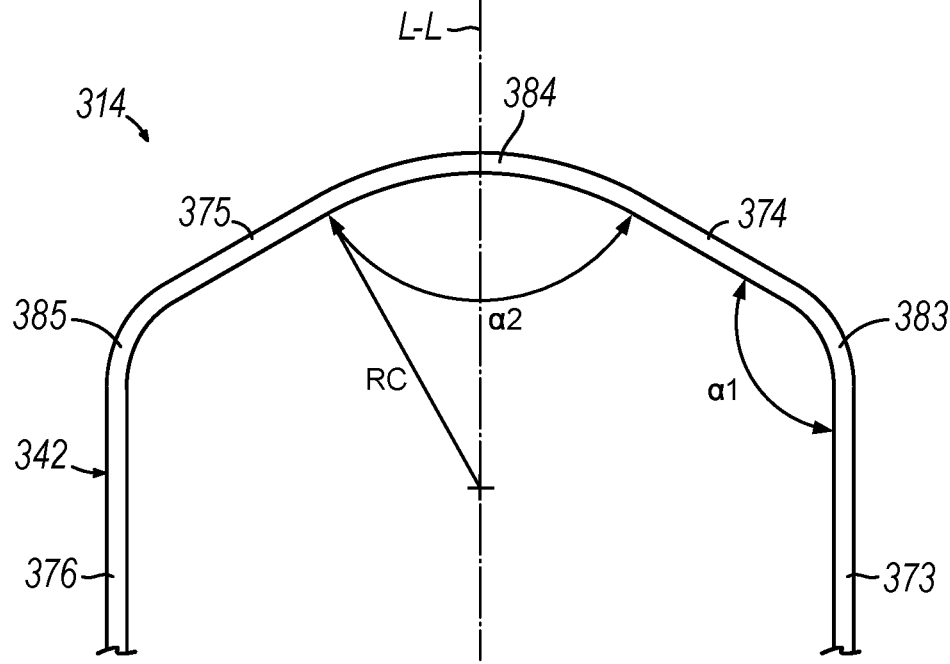
FIG. 4 illustrates a partial front plan view of the outer loop member of the end effector of FIG. 1.

As shown in FIG. 4, fourth linear segment (374) is oriented at a first angle ($\alpha 1$) relative to third linear segment (373), such that distalmost arch (325) may likewise be oriented at first angle ($\alpha 1$) relative to first outermost spine member (324a). First angle ($\alpha 1$) may be obtuse. In some versions, first angle ($\alpha 1$) may be approximately 120 degrees. While not shown, fifth linear segment (375) may also be oriented at first angle ($\alpha 1$) relative to sixth linear segment (376), such that distalmost arch (325) may likewise be oriented at first angle ($\alpha 1$) relative to second outermost spine member (324b). In the example shown, fifth linear segment (375) is oriented at a second angle ($\alpha 2$) relative to fourth linear segment (374), such that fourth curved segment (384) subtends second angle ($\alpha 2$). Second angle ($\alpha 2$) may be obtuse. In some versions, second angle ($\alpha 2$) may be approximately 120 degrees. In addition, or alternatively, first and second angles ($\alpha 1$, $\alpha 2$) may be the same as each other. For example, first and second angles ($\alpha 1$, $\alpha 2$) may each be approximately 120 degrees. As shown, fourth curved segment (384) has a radius of curvature (RC). In some versions, radius of curvature (RC) may be selected to provide distalmost arch (325) with a substantially increased arc length. For example, radius of curvature (RC) of fourth curved segment (384) may be approximately 5 mm.

By forming third linear segment (373) and sixth linear segment (376) integrally with each other as a unitary (e.g., monolithic) portion of structural member (342) of outer loop member (314) such that outermost spine members (324a, 324b) are likewise integrally formed with each other, and/or by providing fourth curved segment (384) with an increased arc length such that distalmost arch (325) likewise has an increased arc length, outer loop member (314) may be configured to distribute stress substantially evenly across a substantially large region including outermost spine members (324a, 324b) and distalmost arch (325), such as during transitioning of outer loop member (314) from an expanded state to a collapsed state upon entry into tubular sheath (13). In this manner, outer loop member (314) may avoid experiencing highly concentrated stress in localized regions such as at or near respective middle portions of outermost spine members (324a, 324b) and may thereby reduce or eliminate the risk of plastically deforming. For example, outermost spine members (324a, 324b) may be forced to collapse and deform as a unitary body rather than as separate bodies that may otherwise deform independently from each other.

While not shown, distalmost arch (325) may have a varying width to further promote folding of fourth and fifth linear segments (374, 375) and/or fourth curved segment (384) in a desired manner during transitioning of outer loop member (314) from an expanded state to a collapsed state upon entry into tubular sheath (13). For example, fourth and fifth linear segments (374, 375) may each have a first width while fourth curved segment (384) may have a second width less than the first width. In some versions, a smooth transition between such first and second widths may be provided via a taper.

In addition, or alternatively, a cross section of structural member (342) of outer loop member (314) may be configured to provide an optimized balance between in-plane and out-of-plane deformation during transitioning of outer loop member (314) from the expanded state to the collapsed state. For example, the cross section of structural member (342) may be rectangular and may have a width-to-thickness ratio of approximately 1:1 to achieve a balanced fold. In some other versions, the cross section of structural member (342) may be rectangular and may have a width-to-thickness ratio of approximately 2:1, with structural member (342) being twisted about its own central axis at an angle of approximately 45 degrees to achieve a balanced and predictable fold.

Figures 5A, 5B:
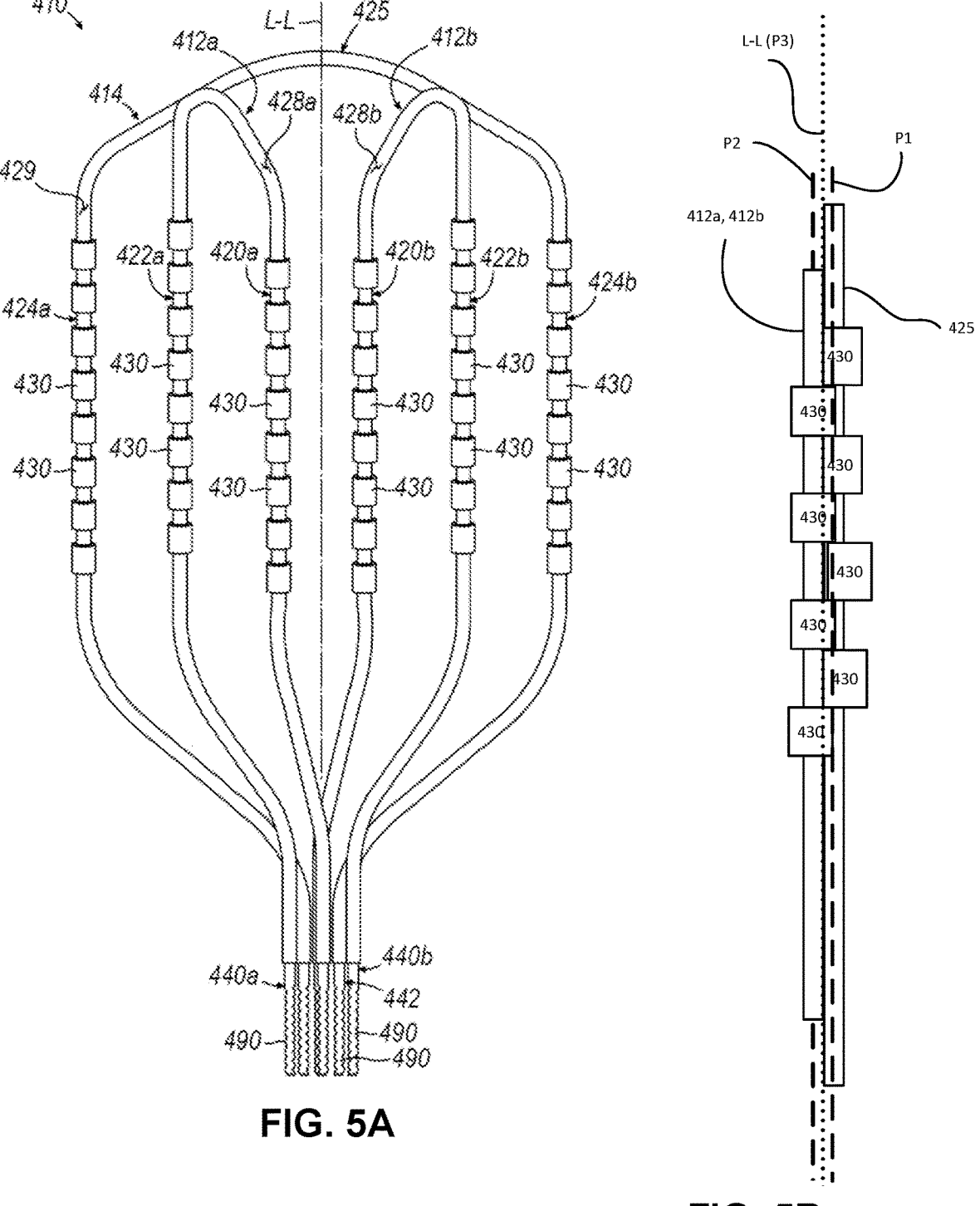
FIG. 5A illustrates a front plan view of another example of an end effector for use with the catheter of FIG. 1, including a pair of inner loop members and an outer loop member having a pair of outermost spines that are integrally formed with each other.
FIG. 5B illustrates a side view of the loops showing first through third planes (P1, P2, P3) due to the arrangement of the loop members of FIG. 5A, which arrangement is also applicable to FIG. 1.

FIG. 5A depicts another example of an end effector (410) that may be incorporated into catheter (10) in place of end effector (310). End effector (410) may be similar to end effector (310) described above except as otherwise described below. In this regard, end effector (410) of this example includes first and second inner loop members (412a, 412b) and an outer loop member (414), which may each extend distally from a base member (not shown) similar to base member (316) and extending along longitudinal axis (L-L). Inner loop members (412a, 412b) each include a corresponding innermost spine member (420a, 420b) and a corresponding intermediate spine member (422a, 422b), while outer loop member (414) includes a pair of outermost spine members (424a, 424b) coupled to each other via a distalmost arch (425).

As shown, inner loop members (412a, 412b) each include a corresponding cover (428a, 428b) while outer loop member (414) includes a corresponding cover (429). Loop members (412a, 412b, 414) also each include a corresponding plurality of sensing electrodes (430) disposed on an outer surface of the respective cover (428a, 428b, 429).

Each inner loop member (412a, 412b) has a corresponding elongated structural member (440a, 440b) extending continuously through the length of the respective inner loop member (412a, 412b) to and from the base member, while outer loop member (414) has an elongated structural member (442) extending continuously through the length of outer loop member (414) to and from the base member. Structural members (440a, 440b) of inner loops (412a, 412b) may each be configured and operable in manners similar to those described above in connection with FIG. 2, and structural member (442) of outer loop (414) may be configured and operable in manners similar to those described above in connection with FIGS. 2 and 4. In the example shown, structural members (440a, 440b, 442) each include serrations (490) along their respective proximal linear segments to allow structural members (440a, 440b, 442) to be locked to each other and/or overmolded into the base member.

II. Examples of Combinations That Are Within the Scope of the Inventions

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A catheter for electrophysiology applications, comprising: (a) a shaft extending along a longitudinal axis to a distal end; and (b) an end effector coupled to the distal end of the shaft, the end effector including: (i) a first loop member disposed on a first side of the longitudinal axis, (ii) a second loop member disposed on a second side of the longitudinal axis, and (iii) a third loop member including: (A) a first spine disposed on the first side of the longitudinal axis, the first spine including a first plurality of electrodes, the first spine being positioned radially outwardly of the first loop member relative to the longitudinal axis, and (B) a second spine disposed on the second side of the longitudinal axis, the second spine including a second plurality of electrodes, the second spine being positioned radially outwardly of the second loop member relative to the longitudinal axis.

Example 2

The catheter of Example 1, the third loop member being symmetrical relative to the longitudinal axis.

Example 3

The catheter of any of Examples 1 through 2, the first and second loop members each being asymmetrical.

Example 4

The catheter of any of Examples 1 through 3, the first and second loop members being mirror images of each other relative to the longitudinal axis.

Example 5

The catheter of any of Examples 1 through 4, the third loop member including a distal arch extending between the first and second spines.

Example 6

The catheter of Example 5, the third loop member including an elongate structural member at least partially defining each of the first spine, the second spine, and the distal arch.

Example 7

The catheter of Example 6, the elongate structural member including nitinol.

Example 8

The catheter of any of Examples 6 through 7, the elongate structural member including a first linear segment at least partially defining the first spine and a second linear segment at least partially the second spine, the first and second linear segments being integrally formed with each other as a unitary piece.

Example 9

The catheter of any of Examples 6 through 8, the elongate structural member including first and second linear segments at least partially defining the distal arch, the first and second linear segments being oriented at an obtuse angle relative to each other.

Example 10

The catheter of Example 9, the obtuse angle being about 120 degrees.

Example 11

The catheter of any of Examples 6 through 10, the elongate structural member including a curved segment at least partially defining the distal arch.

Example 12

The catheter of Example 11, the curved segment having a radius of curvature of about 5.33 mm.

Example 13

The catheter of any of Examples 6 through 12, the elongate structural member including at least one segment at least partially defining the distal arch, the at least one segment having a varying width.

Example 14

The catheter of any of Examples 1 through 13, the end effector being configured to transition between an expanded state and a collapsed state.

Example 15

The catheter of Example 14, the end effector being resiliently biased to assume the expanded state.

Example 16

The catheter of any of Examples 1 through 15, the first loop member including: a third spine disposed on the first side of the longitudinal axis, the third spine including a first plurality of electrodes, and (B) a fourth spine disposed on the first side of the longitudinal axis, the fourth spine including a second plurality of electrodes; the second loop member including: (A) a fifth spine disposed on the second side of the longitudinal axis opposite the first side, the fifth spine including a third plurality of electrodes, and (B) a sixth spine disposed on the second side of the longitudinal axis, the sixth spine including a fourth plurality of electrodes.

Example 17

The catheter of Example 16, the third spine being positioned radially inwardly of the fourth spine relative to the longitudinal axis, the fifth spine being positioned radially inwardly of the sixth spine relative to the longitudinal axis.

Example 18

The catheter of any of Examples 16 through 17, each of the first, second, third, fourth, fifth, and sixth spines being substantially parallel to each other.

Example 19

A catheter for electrophysiology applications, comprising: (a) a shaft extending along a longitudinal axis to a distal end; and (b) an end effector coupled to the distal end of the shaft, the end effector being configured to transition between an expanded state and a collapsed state, the end effector being resiliently biased to assume the expanded state, the end effector including: (i) a pair of inner loop members each including a respective plurality of electrodes, and (ii) an outer loop member including a respective plurality of electrodes, the outer loop member being positioned radially outwardly of each of the inner loop members relative to the longitudinal axis.

Example 20

A catheter for electrophysiology applications comprising: (a) a main loop extending along a longitudinal axis on a first plane; (b) a second loop extending along the longitudinal axis on one side of the longitudinal axis on a second plane generally parallel to the first plane, the second loop being coupled to the main loop proximate a distal portion of the main loop; and (c) a third loop extending along the longitudinal axis on another side of the longitudinal axis on the second plane, the third loop being coupled to the main loop proximate a distal portion of the main loop.

Example 21

A catheter for electrophysiology applications, comprising: (a) a shaft extending along a longitudinal axis to a distal end; and (b) an end effector coupled to the distal end of the shaft, the end effector including: (i) a first loop member including: (A) a first spine disposed on a first side of the longitudinal axis, the first spine including a first plurality of electrodes, and (B) a second spine disposed on the first side of the longitudinal axis, the second spine including a second plurality of electrodes, (ii) a second loop member including: (A) a third spine disposed on a second side of the longitudinal axis opposite the first side, the third spine including a third plurality of electrodes, and (B) a fourth spine disposed on the second side of the longitudinal axis, the fourth spine including a fourth plurality of electrodes, and (iii) a third loop member including: (A) a fifth spine disposed on the first side of the longitudinal axis, the fifth spine including a fifth plurality of electrodes, the fifth spine being positioned radially outwardly of each of the first and second spines relative to the longitudinal axis, and (B) a sixth spine disposed on the second side of the longitudinal axis, the sixth spine including a sixth plurality of electrodes, the sixth spine being positioned radially outwardly of each of the third and fourth spines relative to the longitudinal axis.

Example 22

The catheter of Example 21, the first spine being positioned radially inwardly of the second spine relative to the longitudinal axis, the third spine being positioned radially inwardly of the fourth spine relative to the longitudinal axis.

Example 23

The catheter of any of Examples 21 through 22, the first and second loop members each being asymmetrical, the third loop member being symmetrical relative to the longitudinal axis.

Example 24

The catheter of any of Examples 21 through 23, each of the first, second, third, fourth, fifth, and sixth spines being substantially parallel to each other.

The embodiments described above are cited by way of example, and the present invention is not limited by what has been particularly shown and described hereinabove. Rather, the scope of the invention includes both combinations and sub combinations of the various features described and illustrated hereinabove, as well as variations and modifications thereof which would occur to persons skilled in the art upon reading the foregoing description and which are not disclosed in the prior art.

III. Miscellaneous

Any of the instruments described herein may be cleaned and sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, hydrogen peroxide, peracetic acid, and vapor phase sterilization, either with or without a gas plasma, or steam.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A catheter for electrophysiology applications, comprising:
   a shaft extending along a longitudinal axis to a distal end; and
   an end effector coupled to the distal end of the shaft, the end effector comprising first, second, and third loop members,
   the third loop member comprising:
      a first spine segment disposed on a first side of the longitudinal axis of the shaft and comprising a first plurality of electrodes, and
      a second spine segment disposed on a second side of the longitudinal axis of the shaft and comprising a second plurality of electrodes,
   the first loop member comprising third and fourth spine segments both disposed on the first side of the longitudinal axis of the shaft, the first spine segment of the third loop member being positioned radially outwardly of the third and fourth spine segments of the first loop member relative to the longitudinal axis of the shaft, and
   the second loop member comprising fifth and sixth spine segments both disposed on the second side of the longitudinal axis of the shaft, the second spine segment of the third loop member being positioned radially outwardly of the fifth and sixth spine segments of the second loop member relative to the longitudinal axis of the shaft.

2. The catheter of claim 1, the third spine segment of the first loop member including a third plurality of electrodes, the fourth spine segment of the first loop member including a fourth plurality of electrodes, the fifth spine segment of the second loop member including a fifth plurality of electrodes, and the sixth spine segment of the second loop member including a sixth plurality of electrodes.

3. The catheter of claim 1, the third loop member being symmetrical relative to the longitudinal axis, the third loop member defining a first plane that extends through the third loop member.

4. The catheter of claim 3, the first and second loop members each being asymmetrical, the first and second loop members defining a second plane that extends through the first and second loop members, the second plane being spaced from the first plane.

5. The catheter of claim 1, the first and second loop members being mirror images of each other relative to the longitudinal axis of the shaft.

6. The catheter of claim 1, the third loop member including a distal arch extending between the first and second spine segments.

7. The catheter of claim 6, the third loop member including an elongate structural member at least partially defining each of the first spine segment, the second spine segment, and the distal arch.

8. The catheter of claim 7, the elongate structural member including nitinol.

9. The catheter of claim 7, the elongate structural member including a first linear segment at least partially defining the first spine segment and a second linear segment at least partially defining the second spine segment, the first and second linear segments being integrally formed with each other as a unitary piece.

10. The catheter of claim 7, the elongate structural member including first and second linear segments at least partially defining the distal arch, the first and second linear segments being oriented at an obtuse angle relative to each other.

11. The catheter of claim 10, the obtuse angle being about 120 degrees.

12. The catheter of claim 7, the elongate structural member including a curved segment at least partially defining the distal arch.

13. The catheter of claim 12, the curved segment having a radius of curvature of about 5 mm.

14. The catheter of claim 7, the elongate structural member including at least one structural segment at least partially defining the distal arch, the at least one structural segment having a varying width.

15. The catheter of claim 1, the end effector being configured to transition between an expanded state and a collapsed state.

16. The catheter of claim 15, the end effector being resiliently biased to assume the expanded state.

17. The catheter of claim 1, each of the first, second, third, fourth, fifth, and sixth spine segments being substantially parallel to each other.

18. A catheter for electrophysiology applications, comprising:

(a) a shaft extending along a longitudinal axis to a distal end; and (b) an end effector coupled to the distal end of the shaft, the end effector being configured to transition between an expanded state and a collapsed state, the end effector being resiliently biased to assume the expanded state, the end effector including:

(i) a pair of inner loop members each including a respective plurality of electrodes, a first one of the inner loop members comprising first and second spine members both disposed on a first side of the longitudinal axis of the shaft, and a second one of the inner loop members comprising third and fourth spine members both disposed on a second side of the longitudinal axis of the shaft, and (ii) an outer loop member including a respective plurality of electrodes, the outer loop member being positioned radially outwardly of each of the inner loop members relative to the longitudinal axis.

19. The catheter of claim 1, the third loop member defining a first plane that extends through the third loop member, the first and second loop members defining a second plane that extends through the first and second loop members, the second plane being spaced from the first plane.

20. A catheter for electrophysiology applications comprising:

(a) a main loop extending along a longitudinal axis on a first plane;

(b) a second loop extending generally parallel to the longitudinal axis and comprising first and second spine members both positioned on one side of the longitudinal axis on a second plane generally parallel to the first plane, the second loop being coupled to the main loop proximate a distal portion of the main loop; and (c) a third loop extending generally parallel to the longitudinal axis and comprising third and fourth spine members both positioned on another side of the longitudinal axis on the second plane, the third loop being coupled to the main loop proximate the distal portion of the main loop.

* * * * *